US00PP22016P2

(12) United States Plant Patent
Uebelhart

(10) Patent No.: US PP22,016 P2
(45) Date of Patent: Jul. 5, 2011

(54) ***GAILLARDIA* PLANT NAMED 'FANCY WHEELER'**

(50) Latin Name: *Gaillardia aristata*
Varietal Denomination: Fancy Wheeler

(75) Inventor: Georg G. Uebelhart, Schwarmstedt (DE)

(73) Assignee: Jelitto Staudensamen GmbH, Schwarmstedt (DE)

( * ) Notice: Subject to any disclaimer, the term of this patent is extended or adjusted under 35 U.S.C. 154(b) by 0 days.

(21) Appl. No.: 12/803,837

(22) Filed: Jul. 7, 2010

(51) Int. Cl.
*A01H 5/00* (2006.01)

(52) U.S. Cl. ..... Plt./431

(58) Field of Classification Search ..... Plt./431
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of *Gaillardia,* 'Fancy Wheeler', characterized by its large inflorescences with ray florets that exhibit red centers and yellow tips with a clear distinction between the centers and tips, its numerous blooms produced throughout the growing season, and its dwarf, spreading habit and reliably perennial plant habit with hardiness in U.S.D.A. Zones 3 to 9.

2 Drawing Sheets

Botanical classification: *Gaillardia aristata.*
Variety denomination: 'Fancy Wheeler'.

CROSS REFERENCE TO A RELATED APPLICATION

This application is co-pending with a U.S. Plant patent application filed for a plant derived the Inventor's breeding program that is entitled *Gaillardia* Plant Named 'Jazzy Wheeler' (U.S. Plant patent application Ser. No. 12/803,790 pending).

BACKGROUND OF THE INVENTION

The present invention relates to a new and distinct cultivar of *Gaillardia* plant, botanically known as *Gaillardia aristata* 'Fancy Wheeler' and will be referred to hereinafter by its cultivar name, 'Fancy Wheeler'.

'Fancy Wheeler' was derived from a controlled breeding program conducted by the Inventor at a nursery in Schwamstedt, Germany. The breeding program focuses on obtaining new cultivars of *Gaillardia* with compact and floriferous plant habits in a range of inflorescence colors. 'Fancy Wheeler' was selected in 2006 by the Inventor as a single unique plant derived from a cross made in 2005 between unnamed plants from his breeding program with the female parent identified with accession No. G04045 and the male parent identified with accession No. G04051.

Asexual reproduction of the new cultivar was first accomplished via stem cuttings in Lisse, The Netherlands in 2006. The characteristics of this cultivar have been determined to be stable and are reproduced true to type in successive generations.

SUMMARY OF THE INVENTION

The following traits have been repeatedly observed and are determined to be the characteristics of the new cultivar of

*Gaillardia*. These attributes in combination distinguish 'Fancy Wheeler' as unique from all other varieties of *Gaillardia* known to the Inventor.

1. 'Fancy Wheeler' exhibits large inflorescences with ray florets that exhibit red centers and yellow tips with a clear distinction between the centers and tips.
2. 'Fancy Wheeler' is hardy in U.S.D.A. Zones 3 to 9.
3. 'Fancy Wheeler' is reliably perennial with a dwarf, spreading habit.
4. 'Fancy Wheeler' produces numerous blooms throughout the growing season.

'Fancy Wheeler' can be compared to its parents. The female parent differs from 'Fancy Wheeler' in that it lacks bi-colored red and yellow ray florets. The male parent differs from 'Fancy Wheeler' in having bicolor ray florets that are less uniform and lack a clear distinction between the two colors. 'Fancy Wheeler' can also be compared to *Gaillardia* cultivars 'Arizona Sun', 'Primavera' and 'Kobold' (all three unpatented), which have taller habits, smaller blooms and shorter blooming periods, and inflorescences with ray florets that are less uniformly bi-colored. 'Arizona Sun' and 'Primavera' also differ in being less reliably perennial. 'Fancy Wheeler' can also be compared to 'Jazzy Wheeler', which differ in having inflorescences with ray florets having yellow-orange centers.

BRIEF DESCRIPTION OF THE DRAWINGS

The accompanying colored photographs illustrate the overall appearance and distinct characteristics of the new *Gaillardia.* The photographs were taken of plants two years in age as grown outdoors in a 1-gallon container in Lisse, the Netherlands.

The photograph in FIG. 1 is a side view of 'Fancy Wheeler' in bloom.

Figure 1:
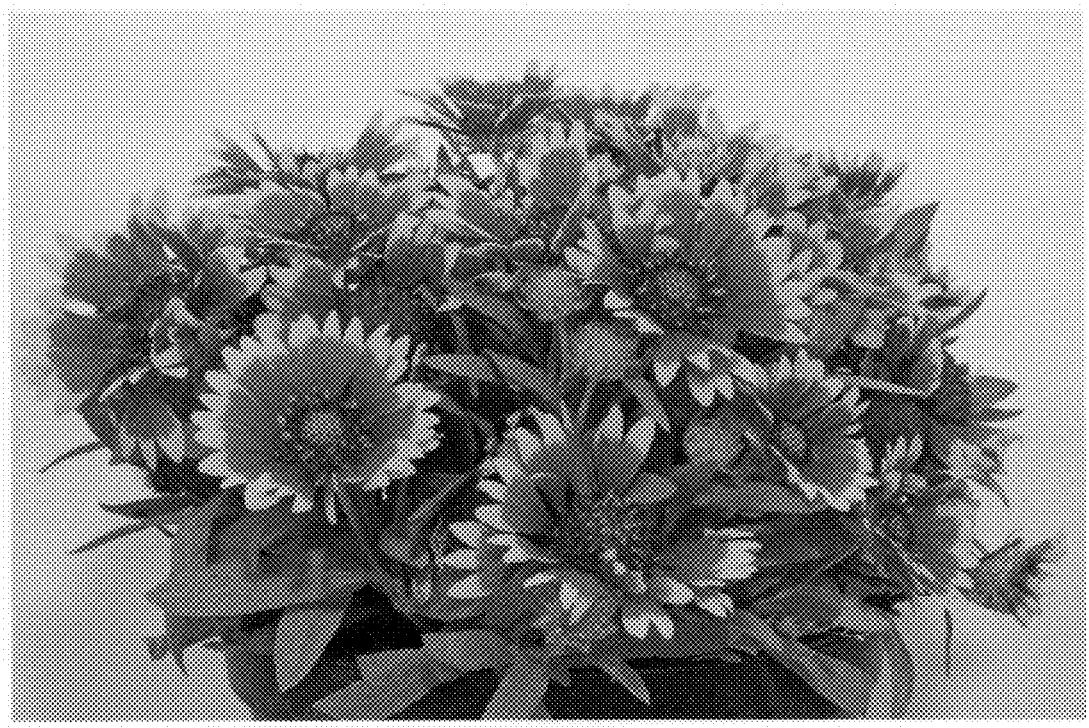
Figure 2:
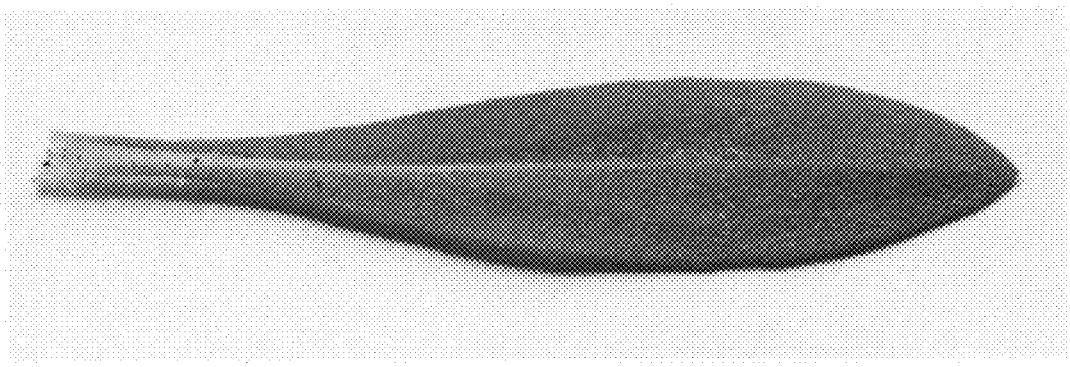
FIG. 2 is a photograph of the upper surface of a single leaf of 'Fancy Wheeler'.
Figure 3:
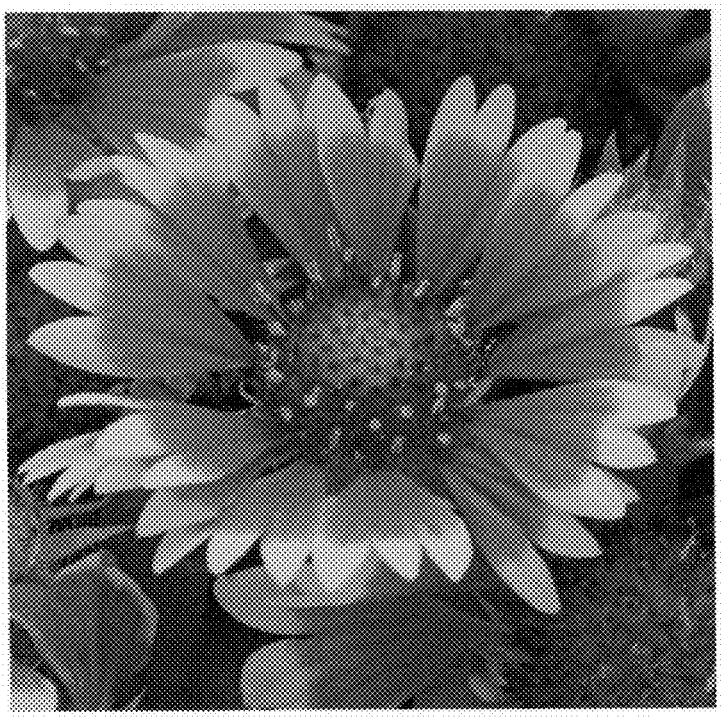

The photograph in FIG. 3 provides a close-up view of an inflorescence of 'Fancy Wheeler'. The colors in the photographs are as close as possible with the digital photography and printing techniques utilized and the color codes in the detailed botanical description more accurately describe the colors of the new *Gaillardia*.

DETAILED BOTANICAL DESCRIPTION

The following is a detailed description of the new cultivar with data collected on three year-old plants that were field grown in Lisse, The Netherlands with average day temperatures ranging between 14° to 32° C. and average night temperatures ranging between 5° and 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season.*—Summer, mid-June to early October in the Netherlands.

*Plant habit.*—Herbaceous perennial, dwarf, globular in overall shape, broad and upright and spreading growth habit.

*Height and spread.*—About 15.6 cm in height and 27.8 cm in width.

*Hardiness.*—U.S.D.A. Zones 3 to 9.

*Diseases resistance.*—No susceptibility or resistance to diseases has been observed.

*Root description.*—Fibrous.

Growth and propagation:

*Propagation.*—Stem cuttings and tissue culture.

*Time from cutting to flowering.*—Average of 20 weeks.

*Crop maintenance.*—No pinching or pruning required.

*Growth rate.*—Low to moderate, 5 cm per month.

Stem description:

*Stem shape.*—Rounded.

*Stem aspect.*—Average 50° from horizontal, ranging from 25° to 90°.

*Stem strength.*—Moderate.

*Stem color.*—145B.

*Stem surface.*—Densely strigullose with strigose hairs averaging 1 mm in length and NN 155D in color.

*Lateral branch length.*—An average of 8.4 cm.

*Lateral branch diameter.*—An average of 2.5 mm.

*Quantity of lateral branches.*—About 47 per plant.

*Internode length.*—Average of 1.1 cm.

*Branching.*—Freely branched.

Foliage description:

*Leaf division.*—Simple.

*Leaf shape.*—Oblanceolate.

*Leaf base.*—Attenuate.

*Leaf apex.*—Broadly acute.

*Leaf margin.*—Entire.

*Leaf venation.*—Pinnate, 144A in color.

*Leaf attachment.*—Sessile.

*Leaf arrangement.*—Alternate.

*Leaf surface.*—Dull and moderately strigullose on upper and lower surfaces, strigose hairs about 0.8 mm in length and NN155D in color.

*Leaf color.*—Young foliage; upper surface 143A, lower surface 138B and 143A, mature foliage; upper surface 138A and 143A, lower surfaces 138A to 138B.

*Leaf size.*—An average of 7.2 cm in length and 1.5 cm in width.

Flower description:

General description:

*Inflorescence type.*—Terminal capitulum with many disc florets, one row of ray florets, and three rows of involucral bracts.

*Rate of flowering.*—Terminal inflorescence opens before lateral inflorescence.

*Lastingness of inflorescence.*—About 2 weeks, persistent.

*Fragrance.*—Faint, slightly sweet.

*Quantity of inflorescences.*—1 per lateral stem, about 95 per plant.

*Inflorescence buds.*—About 7 mm in depth and 1.7 mm in diameter, flattened globular in shape, color 143B with centers 144B to 144C.

*Inflorescence size.*—About 2.7 cm in depth and 6.2 cm in diameter, diameter of disk about 2.1 cm.

*Receptacle.*—Rounded with flattened base, about 3 mm in depth and 4 mm in diameter, 157D in color.

*Peduncle.*—Round in shape, moderately strong, 145B in color, apex 145C to 145D in color, about 3.8 cm in length and 2 mm in diameter, surface is densely strigullose with strigose hairs about 1 mm in length and NN155D in color.

*Involucral bracts (phyllaries).*—24 per inflorescence, arranged in 3 rows, lanceolate in shape, acute apex, broadly cuneate base, margin entire and covered in villous hairs about 1.5 mm in length and NN155D in color, upper surface dull and smooth, lower surface densely pubescent with hairs 0.3 mm in length NN155D in color, 138B in color on upper and lower surface, about 1.1 cm in length and 3.5 mm in width.

Ray florets (capitulate):

*Number.*—Average of 13.

*Arrangement.*—Rotate, 1 whorl.

*Shape.*—Obovate.

*Aspect.*—Slightly upright at an angle of 20° from horizontal.

*Size.*—Average of 3 cm in length and 1.5 cm in width.

*Ray floret apex.*—Three-lobed.

*Ray floret base.*—Cuneate.

*Ray floret margins.*—Entire.

*Ray floret texture.*—Upper and lower surface; smooth, slightly ribbed lengthwise and sparsely puberulent at base with hairs 0.8 mm in length and 60C to 60D in color.

*Color.*—Opening; Upper surface a blend of N34A and 185A, apex 15A, lower surface a blend of 178B and 181A, apex 15A to 15B, fully open; upper surface N34A, apex 15A, lower surface a blend of 178B and 181A, apex 15A to 15B, senescing; upper surface N34C, apex 13A to 13B, lower surface 179C, apex 13A to 13B.

Disk florets (perfect):

*Quantity.*—Average of 75.

*Shape.*—Tubular.

*Arrangement.*—Spiral concentric towards center of disc.

*Disk floret apex.*—Free, narrowly acute, entire margin.

*Disk floret base.*—Fused.

*Disk floret texture.*—Upper surface; smooth, slightly glossy, lower surface; strongly hirsute, slightly glossy.

*Size.*—About 1.1 cm in length and 3 mm in width.

*Color.*—Upper and lower surfaces; N34A, apex 187A, mid-section 145B to 145C, base 145D.

Reproductive organs:

*Presence.*—Disk flowers are perfect, ray flowers are carpellate.

*Gynoecium.*—1 pistil per disk and ray floret, 1 cm in length, stigma decurrent and 200A in color, style 6 mm in length and 200A in color, ovary 145D in color.

*Androecium.*—5 stamens per disk floret, filament 3 mm in length and 145C to 145D in color, anther linear in shape, 4 mm in length and 15B in color becoming 200A to 200B towards apex, pollen moderate to abundant in quantity and 14B in color.

*Fruit and seed.*—No fruits or seeds observed to date.

It is claimed:

1. A new and distinct cultivar of *Gaillardia* plant named 'Fancy Wheeler' as herein illustrated and described.

* * * * *